United States Patent [19]

Avakian et al.

[11] Patent Number: 5,594,053
[45] Date of Patent: Jan. 14, 1997

[54] AROMATIC CYCLIC BISPHOSPHITE ESTERS AND POLYMERIC COMPOSITIONS THEREOF

[75] Inventors: Roger W. Avakian, Parkersburg; Vaikunth S. Prabhu, Vienna, both of W. Va.; William P. Enlow; Carloss L. Gray, both of Belpre, Ohio

[73] Assignee: General Electric Company, Pittsfield, Mass.

[21] Appl. No.: 589,231

[22] Filed: Jan. 22, 1996

[51] Int. Cl.$^6$ ............... C08K 5/527; C07F 9/6574
[52] U.S. Cl. ............................... 524/120; 558/78
[58] Field of Search ................ 524/120; 558/78

[56] References Cited

U.S. PATENT DOCUMENTS

| | | |
|---|---|---|
| 2,974,158 | 3/1961 | Lanham ................. 558/79 |
| 3,039,993 | 6/1962 | Friedman . |
| 3,056,823 | 10/1962 | Hechenbleikner et al. . |
| 3,264,247 | 8/1966 | Friedman . |
| 3,281,381 | 10/1966 | Hechenbleikner et al. . |
| 3,305,520 | 2/1967 | Fritz et al. . |
| 3,305,526 | 2/1967 | Guttag . |
| 3,342,767 | 9/1967 | Buckley . |
| 3,415,906 | 12/1968 | Shepard et al. . |
| 3,437,720 | 4/1969 | Guttag . |
| 3,441,633 | 4/1969 | Friedman . |
| 3,467,733 | 9/1969 | Dever et al. . |
| 3,482,002 | 12/1969 | Dever et al. . |
| 3,483,147 | 12/1969 | Friedman . |
| 3,488,407 | 1/1970 | Schall . |
| 3,509,091 | 4/1970 | Cleveland et al. . |
| 3,558,554 | 1/1971 | Kuriyama et al. . |
| 3,646,173 | 2/1972 | Gordon et al. . |
| 3,714,302 | 1/1973 | Dever et al. . |
| 3,794,629 | 2/1974 | Eimers et al. . |
| 3,845,168 | 10/1974 | Guttag . |
| 4,086,304 | 4/1978 | Hutton et al. . |
| 4,154,691 | 5/1979 | Mauric et al. ............ 558/79 |
| 4,196,117 | 4/1980 | Spivack . |
| 4,220,472 | 9/1980 | Mauric et al. ............ 558/79 |
| 4,276,233 | 6/1981 | Markezich et al. . |
| 4,318,845 | 3/1982 | Spivack et al. . |
| 4,405,739 | 9/1983 | Kinson . |
| 4,529,533 | 7/1985 | Chasar . |
| 4,708,979 | 11/1987 | Pedrazzetti et al. . |
| 4,755,546 | 7/1988 | Hechenbleikner et al. . |
| 4,782,170 | 11/1988 | Bae et al. . |
| 4,882,374 | 11/1989 | Wang et al. . |
| 4,956,406 | 9/1990 | Myers et al. . |
| 4,957,954 | 9/1990 | Iizuka et al. . |
| 5,280,057 | 1/1994 | Nesvadba ............... 558/78 |
| 5,414,033 | 5/1995 | Nesvadba ............... 558/78 |

FOREIGN PATENT DOCUMENTS 2087399  5/1982  United Kingdom .

OTHER PUBLICATIONS

*Phosphorus and Sulfur,* (1983) vol. 15, pp. 9–13.

Primary Examiner—Veronica P. Hoke

[57] ABSTRACT

An stabilized thermoplastic composition comprising a stabilizing amount of a phosphite of the formula:

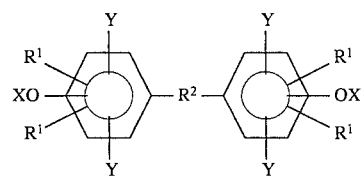

$R_1$ is independently selected from the group consisting of alkyl groups having from 1 to 9 carbon atoms, Y is independently selected from the group consisting of hydrogen, halogen, or alkyl; and the —O—X groups are positioned at the respective ortho- or para- positions with respect to the diphenyl linkage, the remaining ortho- and para- positions with respect to the —O—X linkage being occupied by $R_1$ whereby the —O—X groups are hindered by the presence of at least one $R_1$ group; $R^2$ group is a divalent alkylidene radical having from 1 to 6 carbon atoms or a direct bond; and wherein X has the formula:

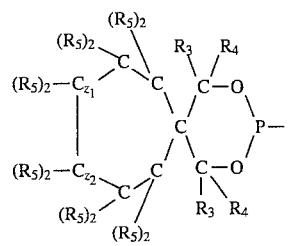

21 Claims, No Drawings

AROMATIC CYCLIC BISPHOSPHITE ESTERS AND POLYMERIC COMPOSITIONS THEREOF

BACKGROUND OF THE INVENTION

1. Field of the Invention

The present invention relates to bisphosphites, and more particularly related to aromatic dicyclic phosphites which contain a neo substituted carbon group and stabilizing compositions and stabilized resin containing such phosphite compositions.

2. Description of the Related Art

U.S. Pat. No. 3,467,733 to Dever et al describes cyclic phosphites and diphosphites, such as bis(1,3,2-dioxaphosphorinanyl-2-oxy)aryl alkanes, and mono- and bis(1,3,2-dioxaphosphorinanyl-2-oxy)benzenes, useful as stabilizers for organic compositions, such a rubber and polyvinyl chloride. Note that column 3, lines 63 to 65 states: It is preferred to employ hydroxy compounds or phenols which do not have hindered 2,6-substitution on the benzene ring.

Many of these phosphites can, however, experience thermal stability problems, hydrolytic stability problems, and/or ultraviolet light discoloration problems. Hence, there still remains a need to enhance the various properties of phosphite compositions.

SUMMARY OF THE INVENTION

The present invention relates to aromatic dicyclic phosphites of the formula:

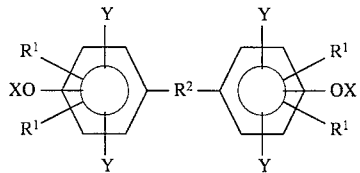

In the above compound, the bisphosphite group includes the OX groups which are the phosphite portion. The OX group is hindered by at least one $R^1$. $R^1$ is independently selected from the group consisting of alkyl groups having from 1 to 9 carbon atoms. Secondary or tertiary branched alkyl groups are preferred with tertiary alkyl groups being most preferred. For enhanced hydrolysis resistance, the $R^1$ groups and a phenyl group are positioned at the respective ortho- or para-positions with respect to the OX group. The $R^2$ group is a divalent alkylidene radical having from 1 to 6 carbon atoms or a direct bond. Y is independently selected from the group consisting of hydrogen, halogen, or alkyl of 1 to 9 carbon atoms. X has the following formula:

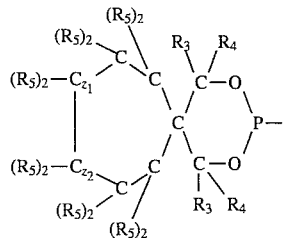

$z_1$ and $z_2$ can be 0 or 1. If $z_1$ and $z_2$ are both 0, the ring is a five member ring. If one of $z_1$ or $z_2$ are 1 and one is 0, the ring is a six member ring. If $z_1$ and $z_2$ are both 1, the ring is a seven member ring. $R_3$, $R_4$ and $R_5$ are independently selected from the group consisting of hydrogen, halogen, or alkyl, preferably an unsubstituted alkyl from 1 to 6 carbon atoms and most preferably from 1 to 3 carbon atoms. Preferably, the $R_3$ groups are hydrogen. It is preferable for the alpha-carbon in the ring structure to include as least one hydrogen substituent. As explained more fully herein, the above phosphite entities are typically formed from 1,3 alkane diols with the beta or 2 position being blocked by alkyl or cyclic alkyl groups.

The phosphites, which are useful to stabilize organic materials against thermal oxidative degradation, exhibit enhanced hydrolytic stability and are resistant to UV yellowing. The present invention further includes an amorphous phosphite composition containing the above phosphite and stabilizing blends therefrom.

DETAILED DESCRIPTION OF THE INVENTION

In the case where a phenyl group is at the para position with respect to the —O—X group, the OX group is hindered at each of the ortho positions by a $R_1$ group. This formula is set forth as follows:

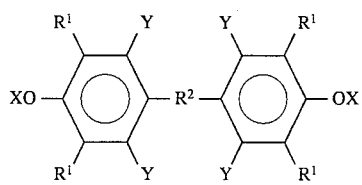

In the case where an $R_1$ group is at the para position to the OX group, one ortho position is occupied by a substituted phenyl group and the other ortho position is occupied by a $R_1$ group. This formula is set forth as follows:

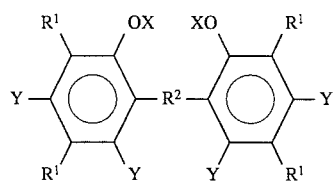

In the aromatic moiety, preferably the $R_1$ groups are as hereinbefore described and even more preferably branched alkyl groups of 3 to 6 carbon atoms, most preferably isopropyl, isobuty, and isoamyl. Sec-butyl and tert-butyl are most preferred. Tert-butyl is most preferred. The $R^2$ group is preferably alkylidene radical having from 1 to 3 carbon atoms or a direct bond. Y is independently selected from the group consisting of hydrogen, halogen, or alkyl of 1 to 9 carbon atoms.

The cyclic phosphite moiety, X, of the phosphite compound as set forth above has the following most preferred formulae:

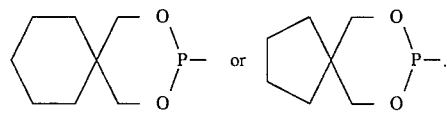

The first step in the production of the phosphite ester of the present invention, is to react an appropriate diol with $PZ_3$ where Z is halogen, preferably Br or Cl. $PCl_3$ is the preferred reactant.

The diols utilized have the beta, beta or the 2,2 positions completely substituted. These diols have the formula:

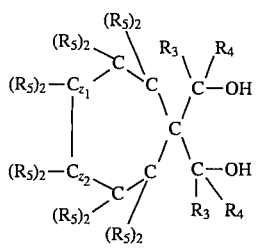

in which $R_{3-5}$ are hereinbefore described.

Alkyl diols that may be used include cycloalkyl-1,1-dimethanol where the cycloalkyl group is from 4 to 7 carbon atoms, such as cyclopentane-1,1-dimethanol, cyclohexane-1,1-dimethanol, and cycloheptane-1,1-dimethanol may be utilized.

The resulting product is an intermediate phosphorohalidite product of the formula:

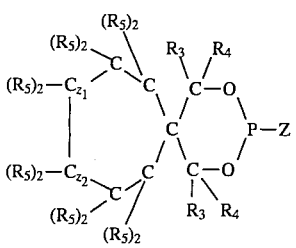

where the R values are as previously described.

The reaction between the diol and $PZ_3$, where Z is halogen, preferably Br or Cl, to form the intermediate phosphorohalidite may be carried out with or without the use of a solvent. Typically $PZ_3$ can be added to the diol or the diol can be added to $PZ_3$. Preferably the $PZ_3$ is added to the diol with the reaction mixture being maintained at a temperature of about 5 to 50 degrees Centigrade. This temperature may be controlled by controlling the rate of $PZ_3$ addition. A slower addition favors lower temperatures. It is preferred to cool the reaction mixture during the addition. A slight excess of stoichiometric amounts of $PZ_3$ is preferably utilized. The reaction is quite exothermic in the absence of a solvent, but a temperature moderating effect is produced by the cooling effect of vigorous HZ evolution. Hence, by effective control $PZ_3$ addition, the reaction may be made self-regulating in the temperature range between 5–15 degrees centigrade.

Desirable solvents that may be utilized are neutral solvents. Typical solvents are toluene, heptane, xylene, methylene chloride, chloroform, and benzene. Preferred solvents are methylene chloride, heptane, or xylene.

After the reaction has gone to completion, the bulk of the by-product HZ such as HCl, may optionally be removed by gently raising the temperature of the product to room temperature to about 50 degrees centigrade. The solvent utilized is removed, typically by application of a vacuum, to yield the remaining intermediate phosphorohalidite product.

To produce the phosphite ester stabilizer of the present invention, the above intermediate phosphorohalidite product is next reacted with a hydroxyaryl compound of the formula:

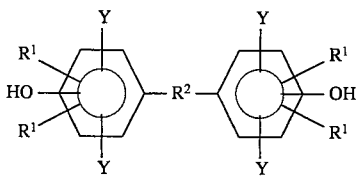

wherein $R^1$, $R^2$ and Y are as described above. Suitable reaction methods are set out in Great Britain Patent 2087399A, U.S. Pat No. 4,318,845 to Spivak et al. issued 1982, and Article in Phosphorous & Sulfur Journal by J. D. Spivak et al. 1983, vol. 15, pp. 9–13, all of which are incorporated herein by reference.

The reaction between the intermediate phosphorohalidite product and the hydroxyaryl compound may be conducted in the same reaction vessel that was employed to produce the crude phosphite ester stabilizer by merely introducing the hydroxyaryl compound into the reactor. The reaction may be carried out at a suitable temperature between 20 to 150 degrees centigrade and preferably between about 35 to about 125 degrees Centigrade. The pressure of the reaction system is maintained between about 50 millimeters mercury absolute to atmospheric pressure. Typical reaction times to substantial completion are from 1 to about 24 hours. Preferably, it is desirable operated under temperature and pressure conditions which will afford the maximum amount of product within time period of about 3 to about 10 hours.

The final proportions of reactants are at least approximately stoichiometric. It is desirable to work with at least a slight stoichiometric excess of one of the reactants.

The reaction is desirable conducted in the presence of a base such as an amine acceptor since $R_1$ is an alkyl group. The amine may be any amine which scavenges hydrogen chloride and/or hydrogen bromide as the case may be. The amine may be aliphatic, cyclic or aromatic. A single amine or a mixture of amines may be used as desired. The cyclic amines usually contain at least about 5 carbon atoms, preferably from 5 to about 10 carbon atoms. Examples include N-methylpyrroidine, N-methylpiperidine, and N-phenylmorpholine, and 1,8-diazabicyclo[5,4,0]undec-7-one. The aromatic amines frequently contain at least 5 carbon atoms with 5 to 15 being preferred. Examples include N,N-dimethylanilines, N,N-dimethylxylidines, pyridine, and alkyl derivative of pyridine. These may include polymer supported amines.

In most cases the amine employed contains at least 3 carbon atoms. Usually the amine contains from 3 to about 18 carbon atoms. The preferred amine acceptors are trialkyl amines with tripropyl amine, tributyl amine, and triheptyl amine being most preferred. When $R_1$ is a tert-alkyl group, such as t-butyl, then a stoichiometric amount of amine acceptor is desirably present.

After completion of the reaction, the amine acceptor present in the reaction mixture may be removed by the addition of a solvent. Typical solvents suitable for this purpose are hindered alcohols with isopropyl alcohol being preferred. The amine acceptor in the reaction mixture is solubilized by the solvent and removed from the reaction mixture to leave a remaining phosphite stabilizer which may be recovered in purified form by distillation, or crystallization. Typically the biphenyl bisphosphite ester may be crystallized or distilled from a suitable organic solvent such as toluene or heptane. It is also contemplated that the biphenyl phosphite may be solubilized by a suitable solvent, removed from the reaction mixture, and then separated from the solvent.

The biphenyl bisphosphites as described above have all the ortho-positions with respect to the —OX group blocked, i.e. either by phenyl or $R_1$, so as to give improved hydrolytic stability. The para- position with respect to the linkage is also blocked by either an $R_1$ group or a phenyl group to inhibit ultraviolet light yellowing of the phosphite. The blockage at the para-position inhibits undesirable side reactions. If hydrogen is present at the para-position, the phosphite may have sensitivity to UV yellowing.

When the phosphite stabilizer is isolated in crystalline form, the present invention contemplates that it may be utilized in solid amorphous form. The amorphous phosphite composition is formed by rapid cooling of melt of the phosphite. Such melt may be a mixture of the phosphite and polyamine which is rapidly cooled to form a solid amorphous phosphite composition. The amorphous nature of composition enhances the hydrolytic stability of the solid composition compared to crystalline composition containing the same constituents, such compositions may additionally contain respective amounts of an amine preferably an aliphatic polyamine.

The amorphous composition is prepared by melting the crystalline phosphite, or a blend of the crystalline phosphite and an amine or other desired ingredients, to form a melt blend. The resulting melt blend is cooled to form an amorphous solid phosphite composition. The process may also involve storing the phosphite for a period in excess of 10 days (possibly in humid conditions (>60% relative humidity)) at ambient temperature, and then compounding the phosphite composition with a thermoplastic polymer such as a polyolefin, for example polypropylene for thermal oxidative stability thereof.

The amorphous stabilizer composition of the present invention preferably comprises at least 50 percent by weight of the phosphite based on the total weight of the stabilizer composition, more preferably comprises from 80 percent by weight to 99.9 percent by weight of the phosphite based on the total weight of the stabilizer composition, more preferably from 90 to 99.8 percent by weight thereof, more preferably from 95 to 99.5 percent by weight thereof, and most preferably from 97 to 99 percent by weight thereof.

A preferred additive is an amine. The amine is preferably present at a level of from 0.1 to 10 percent by weight based on the total weight of the stabilizer composition, more preferably from 0.2 to 10 percent by weight thereof, more preferably present at a level of from 0.6 to 5 percent by weight thereof, and most preferably from 1 to 3 percent by weight thereof. Such stabilizer amine compositions are preferably in the form of amorphous (non-crystalline) particles, such as powders and pellets.

The preferred amine additives are polyamines, and more preferably aliphatic polyamines. The aliphatic polyamine preferably has a boiling point of greater than 175° C., more preferably greater than 190° C., and most preferably greater than 200° C. The aliphatic polyamine may contain primary, secondary or tertiary amine groups. Preferably the amine groups are primary amine groups. The polyamine may contain 2, 3 or more amine groups, and in other words may be a diamine, triamine or greater polyamine amine. The preferred polyamines are aliphatic primary diamines of the formulas $$H_2N-R^{10}-NH_2$$

wherein $R^{10}$ is selected from $C_6$ to $C_{10}$ divalent alkyl groups, and more preferably the diamine is selected from 1,6 diaminohexane and 1,10-diaminodecane. Suitable aliphatic secondary diamines may be represented by the general formula:

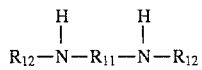

wherein $R^{11}$ is selected from $C_1$ to $C_{10}$ divalent alkyl groups and $R^{12}$ is selected from $C_1$ to $C_{30}$ monovalent alkyl group. Suitable aliphatic tertiary diamines may be represented by the general formula

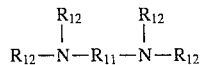

wherein $R^{11}$ and $R^{12}$ are defined as above. Most preferably the polyamine is an aliphatic primary diamine. The amines may also be monoamines and hydroxylamines such as triisopropanolamine, and $R^{12}NH_2$, $R^{12}_2NH$, $R^{12}_3N$, $R^{12}_2NOH$.

The stabilizer composition preferably contains less than 10 percent by weight of other materials, and more preferably less than 5 percent by weight, and most preferably less than 1 percent by weight additional ingredients.

Other ingredients may be polymeric materials and other organic materials such as waxes, synthetic and petroleum dried lubricating oils and greases; animal oils such as for example fat, tallow, lard, cod liver oil, sperm oil; vegetable oil such as caster, linseed, peanut, cod seed, and the like; fuel oil, diesel oil, gasoline, and the like. In other words, the stabilizer composition, is preferably substantially free of other materials, in other words, containing less than 1 percent of other organic materials, and more preferably is free of other organic materials. Optionally, the stabilizer composition is essentially free of monoamines, such as triisopropylamine. The compositions of the present invention are preferably amorphous to ensure homogeneity of the compositions. The present compositions are preferably obtained by melt mixing rather than simple mechanical blending or solution blending, and surprisingly and unexpectedly the compositions made by melt mixing show superior hydrolytic stability over similar compositions made by simple mechanical (dry) or solution blending.

The present invention also is a stabilized polymer composition which includes an effective amount of the phosphite described above. An amount of the phosphite of the invention is considered to be an "effective amount" when the polymer composition containing the phosphite of the invention shows improved stability in any of its physical or color properties in comparison to an analogous polymer composition which does not include a phosphite of the invention. In most polymer compositions, however, it will be preferred that the phosphites be present in an amount equal to about 0.01 to about 2 parts by weight per 100 parts by weight resin (phr). Amounts of about 0.01 to about 1 phr are more preferred, although most compositions will contain about 0.025 phr or more. The polymer composition may be thermoset in nature including unsaturated polyesters, phenolics, epoxy, urethanes, coating resins and crosslinkable latexes.

The polymer may also be any thermoplastic known in the art, such as polyesters, polyurethanes, polyalkylene terephthalates, polysulfones, polyimides, polyphenylene ethers, styrenic polymers, polycarbonates, acrylic polymers, polyamides, polyacetals, halide containing polymers and polyolefin homopolymers and copolymers. Mixtures of different polymers, such as polyphenylene ether/styrenic resin blends, polyvinyl chloride/ABS or other impact modified polymers, such as methacrylonitrile and alphamethylstyrene containing ABS, and polyester/ABS or polycarbonate/ABS and polyester plus some other impact modifier may also be used. Such polymers are available commercially or may be made by means well known in the art. However, the phosphites of the invention are particularly useful in thermoplastic polymers, such as polyolefins, polycarbonates, polyesters, polyphenylene ethers and styrenic polymers, due to the extreme temperatures at which thermoplastic polymers are often processed and/or used.

Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefines with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidenenorbornene; as well as mixtures of such copolymers and their mixtures with polymers mentioned above, for example polypropylene/ethylene propylene-copolymers, LDPE/EVA, LDPE/EAA, LLDPE/EVA and LLDPE/EAA.

Thermoplastic polymers may also include styrenic polymers, such as polystyrene, poly-(p-methylstyrene), poly-(α-methylstyrene), copolymers of styrene or α-methylstyrene with dienes or acrylic derivatives, such as, for example, styrene/butadiene, styrene/acrylonitrile, styrene/alkyl methacrylate, styrene/maleic anhydride, styrene/butadiene/ethylacrylate/styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/-butadiene/styrene, styrene/isoprene/styrene, styrene/ethylene/butylene/styrene or styrene/ethylene/propylene styrene. Styrenic polymers may additionally or alternatively include graft copolymers of styrene or alpha-methylstyrene such as, for example, styrene on polybutadiene, styrene on polybutadiene-styrene or polybutadieneacrylonitrile; styrene and acrylonitrile (or methacrylonitrile) on polybutadiene and copolymers thereof; styrene and maleic anhydride or maleimide on polybutadiene; sytrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/-propylene/diene terpolymers, styrene and acrylonitrile on polyacrylates or polymethacrylates, styrene and acrylonitrile on acrylate/butadiene copolymers, as well as mixtures of with the styrenic copolymers indicated above.

Nitrile polymers are also useful in the polymer composition of the invention. These include homopolymers and copolymers of acrylonitrile and its analogs, such as polymethacrylonitrile, polyacrylonitrile, acrylonitrile/-butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be useful. These include resins such as polychloroprene, epichlorohydrin homo-and copolymers, polyvinyl chloride, polyvinyl bromide, polyvinyl fluoride, polyvinylidene chloride, chlorinated polyethylene, chlorinated polypropylene, florinated polyvinylidene, brominated polyethylene, chlorinated rubber, vinyl chloride-vinylacetate copolymers, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride tercopolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate tercopolymer, vinyl chloride-acrylic acid ester copolymers, vinyl chloride-maleic acid ester copolymers, vinyl chloride-methacrylic acid ester copolymers, vinyl chloride-acrylonitrile copolymer and internally platicized polyvinyl chloride.

Other useful thermoplastic polymers include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-2(2,2,4(4-hydroxyphenyl)-propane) terephthalate and polyhydroxybenzoates as well as block-copolyetheresters derived from polyethers having hydroxyl end groups.

Polyamides and copolyamides which are derived from diamines and dicarboxylic acids and/or from aminocarboxylic acids or the corresponding lactams, such as polyamide, 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylene diamine and isophthalic or/and terephthalic acid and optionally an elastomer as modifier, for example poly-2,4,4-trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

Polyolefin, polyalkylene terephthalate, polyphenylene ether and styrenic resins, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

The resulting stabilized polymer compositions of the invention may optionally also contain various conventional additives, such as the following:

1. Antioxidants
1.1 Alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(alphamethylcyclohexyl)-4,6 dimethylphenol, 2,6-di-octadecyl-4-methylphenol, 2,4,6,-tricyclohexyphenol, 2,6-di-tert-butyl-4-methoxymethylphenol.

1.2 Alkylated hydroquinones, for example, 2,6-di-tert-butyl-4methoxyphenol, 2,5-di-tert-butyl-hydroquinone, 2,5-di-tert-amylhydroquinone, 2,6-diphenyl-4octadecyloxyphenol.

1.3 Hydroxylated thiodiphenyl ethers, for example, 2,2'-thio-bis-(6-tert-butyl-4-methylphenol), 2,2'-thio-bis-(4-octylphenol), 4,4'-thio-bis-(6-tert-butyl-3-methylphenol), 4,4'-thio-bis-(6-tert-butyl-2-methylphenol).

1.4 Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(alpha-methylcyclohexyl(phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(alpha-methylbenzyl)-4-nonylphenol), 2,2'-methylene-bis-(6-(alpha,alpha-dimethylbenzyl)-4-nonyl-phenol). 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane. 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4-hydroxy-5-methylphenyl)-dicyclopentadiene, di-(2-(3'-tert-butyl-2'hydroxy-5'methylbenzyl)-6-tert-butyl-4-methylphenyl)terephthalate, and other phenolics such as mono-acrylate esters of bisphenols such as ethylidiene bis-2,4-di-t-butyl phenol monoacrylate ester.

1.5 Benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercaptoacetate, bis-(4-tert-butyl-3-hydroxy-2,6-dimethylbenzyl)dithiol-terephthalate. 1,3,5-tris-(3,5-di-tert-butyl-4-hydroxybenzyl)isocyanurate. 1,3,5-tris-(4-tert-butyl-3-hydroxy-2,6-dimethylbenzyl)isocyanurate, dioctadecyl 3,5-di-tert-butyl-4-hydroxybenzyl-phosphonate, calcium salt of monoethyl 3,5-di-tert-butyl-4-hydroxybenzylphosphonate, 1,3,5-tris-(3,5-dicyclohexyl-4-hydroxybenzyl) isocyanurate.

1.6 Acylaminophenols, for example, 4-hydroxy-lauric acid anilide, 4-hydroxy-stearic acid amilide, 2,4-bis-octylmercapto-6-(3,5-tert-butyl-4-hydroxyanilino)-s-triazine, octyl-N-(3,5-di-tert-butyl-4-hydroxyphenyl)carbamate.

1.7 Esters of beta-(3,5-di-tert-butyl-4-hydroxyphenol)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, di-hydroxyethyl oxalic acid diamide.

1.8 Esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thidiethyleneglycol, dihydroxyethyl oxalic acid diamide.

1.9 Esters of beta-(5-tert-butyl-4-hydroxy-3-methylphenyl) propionic acid with mono-or polyhydric alcohols, e.g., with methanol, diethylene glycol, octadecanol, triethylene glycol, 1,6-hexanediol, pentaerythritol, neopentyl glycol, tris(hydroxyethyl) isocyanurate, thiodiethylene glycol, N,N-bis(hydroxyethyl) oxalic acid diamide.

1.10 Amides of beta-(3,5-di-tert-butyl-4-hydroxyphenol)-propionic acid for example, N,N'-di-(3,5-di-tert-butyl-4-hydroxyphenylpropionyl)-hexamethylen-diamine, N,N'-di-(3,5-di-tert-butyl-4-hydroxyphenylpropionyl)trimethylenediamine, N,N'-di-(3,5-di-tert-butyl-4-hydroxyphenylpropionyl)-hydrazine.

2. UV absorbers and light stabilizers.
2.1 2-(2'-hydroxyphenyl)-benzotriazoles, for example, the 5'methyl-,3'5'-di-tert-butyl-,5'-tert-butyl-,5'(1,1,3,3-tetramethylbutyl)-,5-chloro-3',5'-di-tert-butyl-,5-chloro-3'tert-butyl-5'methyl-,3'sec-butyl-5'tert-butyl-,4'-octoxy,3',5'-di-tert-amyl-3',5'-bis-(alpha, alpha-dimethylbenzyl)-derivatives.

2.2 2-Hydroxy-benzophenones, for example, the 4-hydroxy-4-methoxy-,4-octoxy,4-decloxy-,4-dodecyloxy-,4-benzyloxy,4,2',4'-trihydroxy- and 2'hydroxy-4,4'-dimethoxy derivative.

2.3 Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butylphenyl-3,5-di-tert-butyl-4-hydroxybenzoate and hexadecyl-3,5-di-tert-butyl-4-hydroxybenzoate.

2.4 Acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methylindoline.

2.5 Nickel compounds, for example, nickel complexes of 2,2'-thiobis(4-(1,1,1,3-tetramethylbutyl)-phenol), such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands.

2.6 Sterically hindered amines, for example bis(2,2,6,6-tetramethylpiperidyl)-sebacate, bis-(1,2,2,6,6-pentamethylpiperidyl)-sebacate, n-butyl-3,5-di-tert-butyl-4-hydroxybenzyl malonic acid bis(1,2,2,6,6,-pentamethylpiperidyl)ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone). These amines typically called HALS (Hindered Amines Light Stabilizing) include butane teracarboxylic acid 2,2,6-tetramentyl piperidonol esters. Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperdine; and N-(1-hydroxy-2,2,6,6-tetramethyl-piperidin-4-yl)-epsiloncaprolactam.

2.7 Oxalic acid diamides, for examples, 4,4'-dioctyloxy-oxanilide, 2,2'-di-octyloxy-5',5'-di-tert-butyloxanilide, 2,2'-di-dodecyloxy-5',5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'ethyl-5,4-di-tert-butyloxanilide and mixtures of ortho- and para-methoxy as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-hydrazine, salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite tristearyl sorbitol triphosphite, and tetrakis(2,4-di-tert-butylphenyl)4,4'-biphenylene diphosphonite.

5. Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, calcium stearoyl lactate, calcium lactate, Zn stearate, Mg stearate, Na ricinoleate and K palmitate, antimony pyrocatecholate or zinc pyrocatecholate, including neutralizers such as hydrotalcites and synthetic hydrotalcites, and Li, Na, Mg, Ca, Al hydroxy carbonates.

8. Nucleating agents, for example, 4-tert butylbenzoic acid, adipic acid, diphenylacetic acid, sodium salt of methylene bis-2,4-dibutylphenyl, cyclic phosphate esters, sorbitol tris-benzaldehyde acetal, and sodium salt of bis(2,4-di-t-butyl phenyl)phosphate.

9. Fillers and reinforcing agents, for example, calcium carbonate, silicates, glass fibers, asbestos, talc, kaolin, mica, barium sulfate, metal oxides and hydroxides, carbon black and graphite.

10. The present invention may also be used in conjunction with aminoxy propanoate derivatives such as methyl-3-(N,N-dibenzylaminoxy)propanoate; ethyl-3-(N,N-dibenzylaminoxy)propanonoate; 1,6-hexamethylene-bis(3-N,N-dibenzylaminoxy)proponoate); methyl-(2-(methyl)-3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

11. Other additives, for example, plasticizers, epoxidized vegetable oils, such as epoxidized soybean oils, lubricants, emulsifiers, pigments, hydroxylamines such as $R_2NOH$ wherein R is a $C_1$ to $C_{30}$ alkyl group, such as propyl or stearyl, optical brighteners, flameproofing agents, anti-static agents, blowing agents and thiosynergists such as dilaurythiodipropionate or distearylthiodipropionate.

12. Nitrones, for example n-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-penta-decyl nitrone, n-octadecyl-alpha-heptadecylnitrone, N-hexadecyl-alpha-heptadecyl nitrone, N-octadecyl-alpha-pentadecy nitrone, N-heptadecyl-alpha-heptadecy nitrone, N-octadecyl-alpha-hexadecyl nitrone, nitrone derived from N,N-dialkylhydroxylamine derived from hydrogenated tallow amine.

Polymeric particles may be coated with the present stabilizer compositions alone or in combination with other stabilizers for stabilization of the polymeric material. Particles may be spherical in shape and may be made by processes such as "Reactor Granule Technology" as disclosed in P. Galli and J. C. Halock, The Reactor Granule—A Unique Technology for the Production of a New Generation of Polymer Blends, Society of Plastics Engineers, Polyolefin III International Conference Feb. 24–27, 1991 and as disclosed in Pedrazzeth et al. U.S. Pat. No. 4,708,979 entitled Process for the Stabilization of Spherically Polymerized Polyolefins issued Nov. 24, 1987 both of which are disclosed herein by reference. Particle formation may be achieved by support Ziegler-Natta Catalyst systems. Suitable commercial processes are known by the trademarks: Spheripol, Addipol and Spherilene.

Olefin polymers may be produced by polymerization of olefins in the presence of Ziegler-Natta catalysts optionally on supports such as but not limited to Mg $Cl_2$, chromium salts and complexes thereof, optionally supported on Silica or other materials. They may also be produced utilizing catalysts based on cyclopentadiene complexes of metals typically complexes of Ti and Zr.

Consistent with the invention, the amorphous stabilizer compositions of the invention may be added to the polymer at any time prior to or during fabrication into articles and may be combined with the polymer by any of a variety of means known in the art, such as by preblending or by being fed directly into fabrication equipment.

The following examples illustrate the present invention.

EXAMPLE 1

A composition of the following formula:

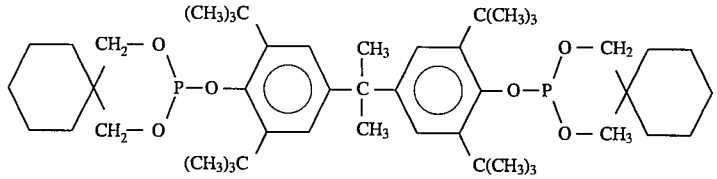

was prepared from 108.69 grams of cyclohexane-1,1-dimethanol, 130.69 grams of phosphorus trichloride and 250 grams of methylene chloride. A 500 ml. 3-necked flask was fitted with a reflux water condenser and an addition funnel. The cyclohexane-1,1-dimethanol and methylene chloride was added to the flask. The flask was cooled to 0–5 degrees Centigrade by placing it into an salt ice bath. The phosphorous trichloride was placed in the addition funnel and was added slowly drop by drop into the reaction flask during a 5 hour period while the temperature was maintained below 10 degrees centigrade. The flask was allowed to warm up to room temperature during a 2 hour period. Methylene chloride was distilled off and the pale yellow color liquid was vacuum distilled at 114°–116° Centigrade for 3.5 mm. of Hg to collect 146.29 grams of pure colorless cyclohexane 1,1-dimethanol chlorophosphite for a yield of 93.04 percent. A 500 ml. 3-necked flask was fitted with a temperature probe, a condenser, and an addition funnel. 22.63 gram of 2,2'-bis(3,5,-di-tert-butyl-4-hydroxyphenyl)propane and 100 grams of tributylamine was added to the flask. The reaction mixture was stirred well with a magnetic stir bar. 23.01 grams of cyclohexane-1,1-dimethyl alcohol chlorophosphite dissolved in approximately 5.0 grams of toluene was placed in the addition funnel and was added into the reaction mixture during a 5 minutes interval. The reaction flask was heated slowly to 70 degrees Centigrade and held for nearly 2 hours at 80–95 degrees Centigrade for 7 hours. The reaction mixture was finally allowed to cool to 60 degrees Centigrade. To separate the reaction product from the amine, 200 ml. of isopropyl alcohol was added into the reaction mixture and stirred. The reaction product was filtered through a sintered glass funnel. The liquid portion containing solubilized amine was separated and a remaining white colored product isolated. Crude mixture was stirred again in 200 ml. of isopropyl alcohol, filtered and dried to isolate 21.0 gram of the product at 52 percent yield. The product had the formula identified above. The melting point was 204–214 degrees Centigrade. A sample crystallized from heptane as white crystalline platelets had a melting point of 214–215.5 degrees Centigrade.

EXAMPLE 2

A composition of the following formula:

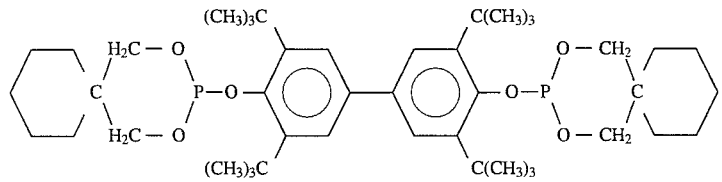

was prepared by following essentially the same procedure as set forth in Example 1, the above compound was prepared from 41.06 grams of tetra-butylated biphenol, 145 grams of tributylamine and 42.14 grams of cyclohexane 1,1-dimethyl alcohol chlorophosphite. 71.66 grams of the above compound was obtained for a yield of 94.91 percent. The product had a melting point greater than 290 degrees Centigrade and a sample crystallized from toluene had a melting point of greater than 290 degrees Centigrade.

EXAMPLE 3

As shown in Table 1, a hydrolytic stability comparison was made by exposing approximately one gram of a sample of each of the phosphites of Example 1 and 2 by placing each sample in a vial and then into a humidity chamber at 80 percent relative humidity at 25 degrees Centigrade. The weight gain was recorded over a period of time. A one percent weight gain was the end point of the study. The compounds remained free flowing after the end of the study. Compounds of Examples 1 and 2 exhibited good high temperature stability and low volatility as evident by TGA studies run under nitrogen atmosphere. The percent weight loss of the starting phosphite was determined as a function of temperature.

TABLE I

TGA* and hydrolytic Studies** of Examples 1 and 2

| Compound | Temperature at 5% Percent Weight Loss | Temperature at 10% Percent Weight Loss | Hydrolytic Stability Hours to 1% wt gain @80% Rel. Humidity |
|---|---|---|---|
| Example 1 | 282 | 312 | 816 |
| Example 2 | 282 | 314 | 2088 |

*DuPont 2100-heating rate of 10° C. minute from room temperature to 500° C. under nitrogen
**Measured 1% weight gain at room temperature at 80% relative humidity as a function of time

EXAMPLE 4

Appropriate amounts of additives were weighed and added with the unstabilized Montell polypropylene as set forth in Table II. The additives were blended and mixed with the resin using a Turbula Blender for 30 minutes. the stabilized resin formulation was extruded at a 100 rpm from 1 inch (2.54 cm) diameter extruder at 260 degrees Centigrade in a Killion Extruder.

After each of the first, third and fifth extrusions, resin pallets were compression molded into 125 mil (3.2. mm) thick plaques at 188 degrees Centigrade and specimen yellowness index (YI) was determined. Low YI values indicate less yellowing. Additionally, the melt flow rate (in grams/10 minutes) was measured (ASTM-D-1238) on pallets after first, third and fifth extrusions. A close melt flow rate after the fifth extrusion which is close to the melt flow rate after the first extrusion is indicative of the superior process stabilization of polypropylene.

TABLE II

| | | | Melt Flow Rate After Extrusion | | | Yellowness Index After Extrusion | | |
|---|---|---|---|---|---|---|---|---|
| CaSt | I-1010 | Ex. I | 1 | 3 | 5 | 1 | 3 | 5 |
| 800 | 800 | — | 5.6 | 6.8 | 8.2 | 3.31 | 4.80 | 5.92 |
| 800 | — | 800 | 4.4 | 4.8 | 5.0 | 2.14 | 4.53 | 6.96 |
| 800 | 800 | 800 | 4.0 | 4.1 | 4.1 | 1.63 | 1.96 | 2.73 |

I-1010 - Irganox ™ 1010, tetrakis{methylene-3-(3,5-di-tert-butyl-4-hydroxyphenyl)propionate}methane, sold by Ciba-Geigy Corp.
U-626 - Ultranox ® phosphite, bis(2,4-di-t-butylphenyl) pentaerythritol, sold by GE Specialty Chemicals, Inc.
U-641 - Ultranox ® phosphite,

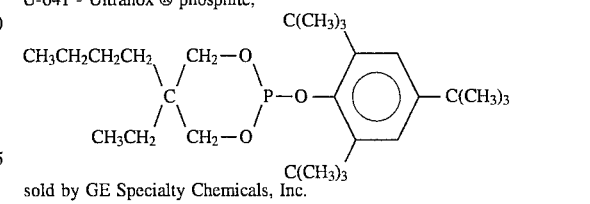

sold by GE Specialty Chemicals, Inc.

EXAMPLE 5

The base formulation comprises 100 parts of unstabilized polyethylene obtained from Chevron with 0.05 parts of I-1010. The phosphite was blended with the resin (See Table III). The resin was blended with the resin for 30 minutes using a Turbula Blender. The stabilized resin formulation was extruded in a Killion extruder at 100 rpm from 1 inch (2.54 cm) diameter opening at 230 degrees Centigrade. After the first extrusion, resin pallets were compression molded into 125 mil (3.2 mm) thick plaques at 188 degrees Centigrade and specimen yellowness index (YI) was determined. Low YI values indicate less yellowing.

TABLE III

| I-1010 | Phosphite U-626 | Phosphite U-641 | Phosphite Example 1 | Yellowness Index |
|---|---|---|---|---|
| 500 | — | — | — | 3.07 |
| 500 | 500 | — | — | −4.06 |
| 500 | — | 500 | — | −1.08 |
| 500 | — | — | 500 | −3.38 |

I-1010 – Irganox™ 1010, tetrakis{methylene-3-(3,5-di-tert-butyl-4-hydroxyphenyl)propionate}methane, sold by Ciba-Geigy Corp.
U-626 - Ultranox ® phosphite, bis(2,4-di-t-butylphenyl) pentaerythritol, sold by GE Specialty Chemicals, Inc.
U-641 - Ultranox ® phosphite,

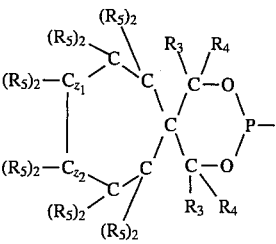

sold by GE Specialty Chemicals, Inc.

We claim:

1. A phosphite of the formula:

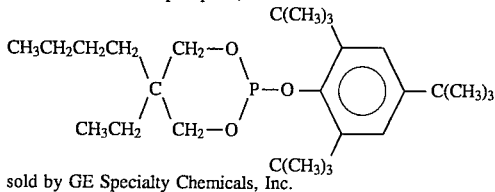

$R_1$ is independently selected from the group consisting of alkyl groups having from 1 to 9 carbon atoms, Y is independently selected from the group consisting of hydrogen, halogen, or alkyl; and the $R_1$ groups and said bi-phenyl linkage is positioned at the respective ortho- or para- positions with respect to the OX group whereby said O—X groups are hindered by the presence of at least one $R_1$ group; $R^2$ group is a divalent alkylidene radical having from 1 to 6 carbon atoms or a direct bond; and wherein X has the formula:

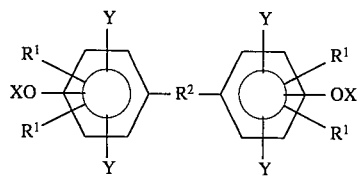

wherein $R_2$ is independently selected from the group consisting of alkyl groups having from 1 to 12 carbon atoms, and $R_3$, $R_4$ and $R_5$ are independently selected from the group consisting of hydrogen, halogen, or alkyl, and z is 0 or 1.

2. The phosphite of claim 1 wherein the phosphite has a formula:

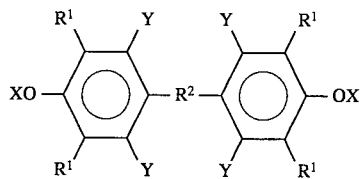

or

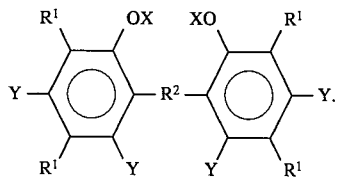

3. The phosphite of claim 1 wherein X has the formula:

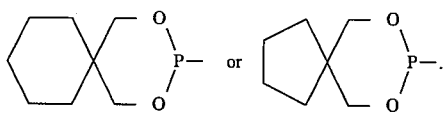

4. The phosphite composition of claim 3 wherein $R_1$ is t-butyl and Y is hydrogen.

5. The phosphite of claim 3 having the formula:

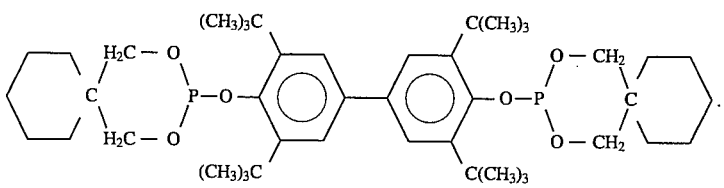

6. The phosphite of claim 3 having the formula:

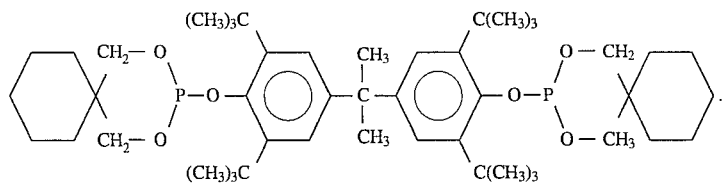

7. A thermoplastic composition comprising a stabilizing amount of a phosphite of the formula:

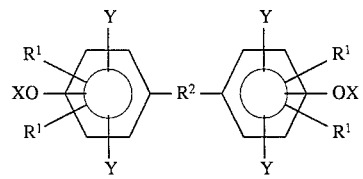

$R_1$ is independently selected from the group consisting of alkyl groups, Y is independently selected from the group consisting of hydrogen, halogen, or alkyl; and the $R_1$ groups and said bi-phenyl linkage is positioned at the respective ortho- or para- positions with respect to the OX group whereby said O—X groups are hindered by the presence of at least one $R_1$ group; and wherein X has the formula:

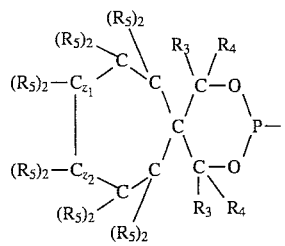

wherein $R_2$ is independently selected from the group consisting of alkyl groups having from 1 to 12 carbon atoms, and $R_3$, $R_4$ and $R_5$ are independently selected from the group consisting of hydrogen, halogen, or alkyl, and z is 0 or 1.

8. A thermoplastic composition of claim 7 wherein the phosphite has a formula:

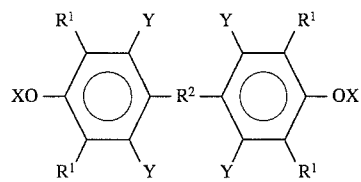

-continued
or

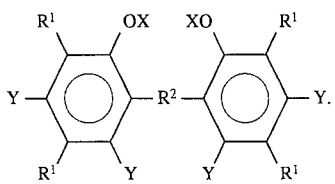

9. A thermoplastic composition of claim 7 wherein X has the formula:

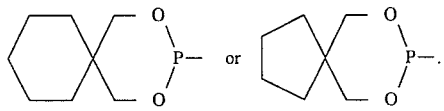

10. A thermoplastic composition of claim 7 wherein $R_1$ is t-butyl and Y is hydrogen.

11. A thermoplastic composition of claim 7 wherein the phosphite has a formula:

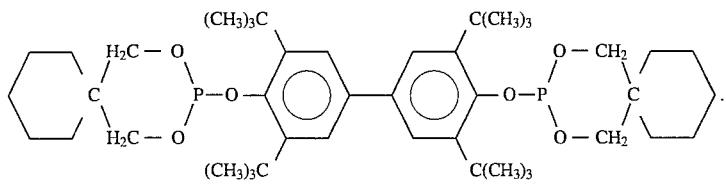

12. A thermoplastic composition of claim 7 wherein the phosphite has a formula:

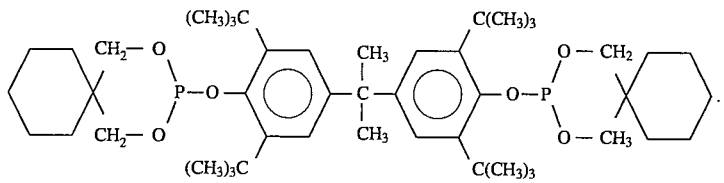

13. A thermoplastic composition comprising a thermoplastic resin and from 0.01 to 1.0 percent by weight of a phosphite composition as claimed in claim 7 based on the total weight of the composition.

14. A thermoplastic composition comprising a thermoplastic resin and from 0.01 to 1.0 percent by weight of a phosphite composition as claimed in claim 7 based on the total weight of the composition.

15. A thermoplastic composition as claimed in claim 7 wherein said thermoplastic resin is selected from the group consisting of polyolefins, polycarbonates, polyesters, polyvinyl chloride and polystrenes.

16. A thermoplastic composition as claimed in claim 7 wherein said thermoplastic resin is polypropylene.

17. A thermoplastic composition as claimed in claim 7 wherein said composition consists essentially of said thermoplastic resin and said phosphite composition.

18. A thermoplastic composition as claimed in claim 7 wherein said composition additionally comprises an antioxidant.

19. A thermoplastic composition as claimed in claim 18 wherein said antioxidant is tetrakis{methylene-3-(3,5-di-tert-butyl-4-hydroxyphenyl)propionate}methane.

20. A thermoplastic composition as claimed in claim 7 wherein said composition additionally comprises a neutralizer.

21. A thermoplastic composition as claimed in claim 19 wherein said neutralizer is calcium stearate.

* * * * *